United States Patent
Prouty, Jr. et al.

(10) Patent No.: US 8,222,205 B2
(45) Date of Patent: *Jul. 17, 2012

(54) PROCESS FOR SOLUBILIZING GLUCAGON-LIKE PEPTIDE 1 COMPOUNDS

(75) Inventors: Walter Francis Prouty, Jr., Indianapolis, IN (US); Joseph Vincent Rinella, Jr., Ypsilanti, MI (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/551,841

(22) Filed: Sep. 1, 2009

(65) Prior Publication Data

US 2011/0053838 A1 Mar. 3, 2011
US 2012/0101034 A9 Apr. 26, 2012

Related U.S. Application Data

(63) Continuation of application No. 10/169,657, filed as application No. PCT/US01/00010 on Jan. 16, 2001, now Pat. No. 7,598,222.

(60) Provisional application No. 60/178,438, filed on Jan. 27, 2000, provisional application No. 60/224,058, filed on Aug. 9, 2000.

(51) Int. Cl.
*A61K 38/26* (2006.01)
*A61K 38/00* (2006.01)
(52) U.S. Cl. ............ 514/7.2; 514/7.3; 530/308; 530/324
(58) Field of Classification Search .................. None
See application file for complete search history.

(56) References Cited

U.S. PATENT DOCUMENTS

| | | | |
|---|---|---|---|
| 6,380,357 B2 | 4/2002 | Hermeling et al. |
| 6,384,016 B1 | 5/2002 | Kaarsholm |
| 6,844,321 B2 | 1/2005 | Arentsen |
| RE41,133 E | 2/2010 | Hermeling et al. |

FOREIGN PATENT DOCUMENTS

| | | |
|---|---|---|
| EP | 0 619 322 | 10/1994 |
| EP | 0 926 159 | 12/1998 |

OTHER PUBLICATIONS

Kim V, et al, "FT-IR and Near-Infared FT-Raman Studies of the Secondary Structure of Insulinotropin in the Solid State: α-Helix to β-Sheet Conversion Induced by Phenol and/or by High Shear Force", *Journal of Pharmaceutical Sciences*, vol. 83, No. 8, Aug. 1994, pp. 1175-1180.

Pridal L, et al, "Absorption of glucagon-like peptide-1 can be protracted by zinc or protamine", *International Journal of Pharmaceutics*, vol. 136, 1996, pp. 53-59.

Senderoff RI, et al, "Consideration of Conformational Transitions and Racemization duging Process Development of Recombinant Glucagon-like Peptide-1", *Journal of Pharmaceutical Sciences*, vol. 87, No. 2, Feb. 1998, pp. 183-189.

*Primary Examiner* — Christine J Saoud
*Assistant Examiner* — Jegatheesan Seharaseyon
(74) *Attorney, Agent, or Firm* — Andrea M. Castetter

(57) ABSTRACT

Disclosed is a method of preparing a GLP-1 compound that is soluble in aqueous solution at pH 7.4 from a GLP-1 compound that is substantially insoluble in aqueous solution at pH 7.4. The insoluble GLP-1 compound is dissolved in aqueous base or in aqueous acid to form a GLP-1 solution. The GLP-1 solution is then neutralized to a pH at which substantially no amino acid racemization of the GLP-1 compounds occurs, after which the soluble GLP-1 compound is isolated from the neutralized solution.

5 Claims, 1 Drawing Sheet

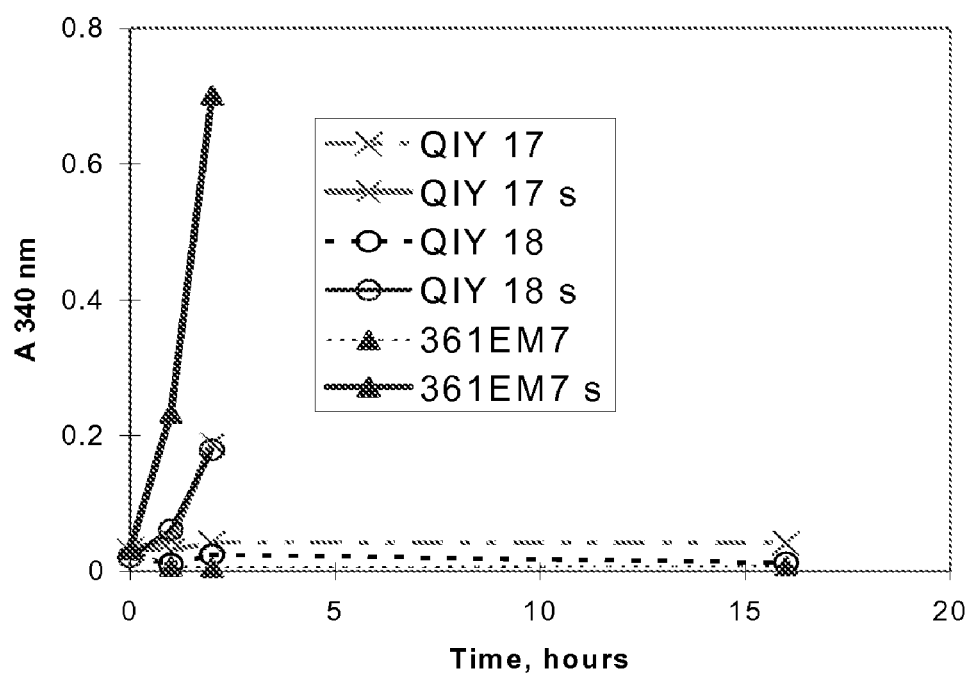

PROCESS FOR SOLUBILIZING GLUCAGON-LIKE PEPTIDE 1 COMPOUNDS

This application is a continuation of U.S. application Ser. No. 10/169,657, now U.S. Pat. No. 7,598,222, filed Jun. 28, 2002, which claims the priority of U.S. Provisional Application Nos. 60/178,438, filed Jan. 27, 2000 and 60/224,058, filed Aug. 9, 2000 and PCT Application No. PCT/US01/00010, filed Jan. 16, 2001.

Glucagon-Like Peptide 1 (GLP-1) is a 37 amino acid peptide that is secreted by the L-cells of the intestine in response to food ingestion. It has been found to stimulate insulin secretion (insulinotropic action), thereby causing glucose uptake by cells and decreased serum glucose levels (see, e.g., Mojsov, S., Int. J. Peptide Protein Research, 40:333-343 (1992)). However, GLP-1(1-37) is poorly active. A subsequent endogenous cleavage between the $6^{th}$ and $7^{th}$ position produces a more potent biologically active GLP-1(7-37)OH peptide. Numerous biologically active GLP-1 analogs and derivatives, referred to herein as "GLP-1 compounds" are also known. For example, GLP-1(7-36)$NH_2$ is a naturally occurring GLP-1 analog in which glycine at the C-terminal has been replaced with —$NH_2$. $Val^8$-GLP-1(7-37)OH is a synthetic GLP-1 (7-37)OH analog in which alanine at position 8 has been replaced with valine; and $Thr^{16}$-$Lys^{18}$-GLP-1(7-37)OH is a synthetic GLP-1(7-37)OH analog in which valine at position sixteen and serine at position eighteen have been replaced with threonine and lysine, respectively. Because of their ability to stimulate insulin secretion, GLP compounds show great promise as agents for the treatment of diabetes, obesity, and related conditions.

GLP-1 compounds can exist in at least two different forms. The first form is physiologically active and dissolves readily in aqueous solution at physiological pH (7.4). In contrast, the second form has little or no insulinotropic activity and is substantially insoluble in water at pH 7.4. Unfortunately, the inactive form is readily produced when aqueous GLP-1 solutions are agitated, exposed to hydrophobic surfaces or have large air/water interfaces. This considerably complicates the production of commercial quantities of active GLP-1 compounds; mixing operations or continuous movement through a pump are common operations in bulk manufacturing processes and these operations cause the agitation, air/water interfaces and/or contact with hydrophobic surfaces that results in the insoluble form.

The realization of the pharmaceutical potential of GLP-1 compounds is dependent on the production of the active form of GLP-1 compounds in commercially viable quantities without contamination with significant quantities of by-products of the inactive form. Thus, there is a critical need for methods of converting in high yield bulk amounts of the inactive insoluble form of GLP-1 compounds to the soluble active form.

It has now been found that the inactive, insoluble form of GLP-1 compounds can be converted into the physiologically active, soluble form by dissolving the inactive form in aqueous base (or in aqueous acid). A further discovery, reported herein, is that the soluble, physiologically active form of GLP-1 compounds can be isolated in high yield and without amino acid racemization or other degradation, provided that the aqueous base solution (or aqueous acid solution) is neutralized to a suitable, less basic (or less acidic) pH. For example, insoluble $Val^8$-GLP-1(7-37)OH was converted to soluble $Val^8$-GLP-1(7-37)OH in high yield and without detectable racemization by dissolving in aqueous sodium hydroxide at pH 12.3, neutralizing to pH 7.0 and isolating the soluble product by filtration and lyophilization (Examples 4 and 6). Based on these discoveries, a method of preparing a soluble, physiologically active GLP-1 compound from its corresponding inactive, insoluble form is disclosed.

The present invention is a method of preparing a GLP-1 compound that is soluble in aqueous solution at pH 7.4 from a GLP-1 compound that is substantially insoluble in aqueous solution at pH 7.4. The insoluble GLP-1 compound is dissolved in aqueous base or in aqueous acid to form a GLP-1 solution. The GLP-1 solution is then neutralized to a pH at which substantially no amino acid racemization of the GLP-1 compounds occurs. The soluble GLP-1 compound is then isolated from the neutralized solution.

In another embodiment, the present invention is a method of converting an insoluble GLP-1 compound in a composition comprising said insoluble GLP-1 compound to a soluble GLP-1 compound. The composition comprising the insoluble GLP-1 compound is dissolved in aqueous acid or in aqueous base to form a GLP-1 solution. The GLP-1 solution is then neutralized to a pH at which substantially no amino acid racemization of the GLP-1 compounds occurs. A composition comprising soluble GLP-1 compound is then isolated from the neutralized solution.

The method of the present invention can be used to convert bulk quantities of the inactive form of GLP-1 compounds to the active form without significant amino acid racemization or other degradation. Therefore, it can be used in commercial processes to prepare active GLP-1 compounds in high yield and in high purity.

BRIEF DESCRIPTION OF THE FIGURES

FIG. 1 is a graph showing the conversion over time of the soluble form of three different lots of $Val^8$-GLP(7-37)OH to the insoluble form in solution (pH 7.4, no salt, 20 mM phosphate, 1 mg/mL protein) with stirring (labeled "s") and without stirring.

A GLP-1 compound is a peptide having from about twenty-five to about thirty-five naturally occurring or modified amino acids and has sufficient homology to GLP-1(7-37)OH such that it exhibits insulinotropic activity. A "modified amino acid" is the amino acid obtained after one or more chemical modifications to a naturally occurring amino acid. Examples of modified amino acids are provided below in the definition of "GLP-1 derivative". "Insulinotropic activity" refers to stimulating insulin secretion in response to food ingestion, thereby causing glucose uptake by cells and decreased serum glucose levels. A wide variety of GLP-1 compounds are known in the art, including GLP analogs, GLP derivatives, biosynthetic GLPs and dipeptidyl-peptidase-IV protected GLPs. The meaning of the terms "GLP analog", "GLP derivative", "biosynthetic GLP" and "dipeptidyl-peptidase-IV protected GLP" are provided herein below.

The solubility of a GLP-1 compound can vary, depending upon how it has been isolated and the manner and length of time it has been stored. For example, the solubility of GLP-1 compounds which have been isolated from solution by crystallization or lyophilization is generally very high. In contrast, the solubility of a GLP-1 compound which precipitates from a solution that contains high salt concentrations, has been exposed to hydrophobic surfaces (e.g., purified by tangential flow filtration) or has large air/water interfaces resulting from, for example, vigorous stirring, is often very low (Example 2). In addition, highly soluble crystals and lyophilized powders of a GLP-1 compound typically show decreased solubility over time. Storage of the compound at low temperatures (e.g., at 0° C.) can slow the conversion to less soluble forms.

The degree to which a GLP-1 compound is soluble in water at physiological pH can be correlated to the insulinotropic activity of the compound. Specifically, the biological activity of a GLP-1 compound increases as it becomes more soluble and decreases as it becomes less soluble. Insulinotropic activity can be assessed by methods known in the art, including using in vivo experiments such as is described in Example 5 and in vitro assays employing pancreatic islet cells or insulinoma cells, as described in EP 619,322 to Gelfand, et al., and U.S. Pat. No. 5,120,712, respectively. The entire teachings of these references are incorporated herein by reference.

The degree to which a GLP-1 compound is soluble in water at physiological pH can also be correlated to absorbances in the infrared spectrum. Specifically, the infrared spectrum of GLP-1 compounds is characterized by absorbances at 1624 $cm^{-1}$, 1657 $cm^{-1}$ and 1696 $cm^{-1}$. The solubility of the GLP-1 compound increases with the intensity of the absorbance at 1657 $cm^{-1}$ and decreases with the intensity of the absorbances at 1624 $cm^{-1}$ and 1696 $cm^{-1}$. Thus, the intensity of these three absorbances will change accordingly as a GLP-1 compound converts to a more soluble or less soluble form (see Example 3).

A GLP-1 compound having a solubility in water at physiological pH (7.4) of at least about 1.0 milligrams per milliliter of water at pH 7.4 is said to be in the "active form" or "soluble form" of the compound. A GLP-1 compound in its active or soluble form is referred to herein as a "soluble GLP-1 compound". Preferably, a soluble GLP-1 compound has a solubility in water at physiological pH of at least about 5.0 milligrams per milliliter. The ratio $A_{1657}/(A_{1624}+A_{1657}+A_{1696})$ is generally at least about 0.60 for GLP-1 compounds in the soluble form and preferably at least about 0.70. A is the absorbance intensity at wavelength n in reciprocal centimeters.

A GLP-1 compound having a solubility in water at physiological pH less than about 0.5 milligrams per milliliter of water is said to be in the "inactive form" or "insoluble form" of the compound. A GLP-1 compound in its inactive or insoluble form is referred to herein as an "insoluble GLP-1 compound". Preferably, an insoluble GLP-1 compound has a solubility in water at physiological pH of less than about 0.1 milligrams per milliliter. The ratio $(A_{1624}+A_{1696})/(A_{1624}+A_{1657}+A_{1696})$ is generally at least about 0.60 for GLP-1 compounds in the soluble form and preferably at least about 0.70. A, is the absorbance intensity at wavelength n in reciprocal centimeters.

It has been reported that the insoluble form of GLP-1 compounds is characterized by the formation of intramolecular and intermolecular beta sheets, which results in compound aggregation and insolubility, whereas the secondary structure of the soluble form is characterized by the presence of alpha helices (see Senderoff et. al. *J. Pharm. Sci.* 87:183 (1998), the entire teachings of which are incorporated herein by reference). The infrared spectrum of the soluble and insoluble forms of GLP-1 compounds is consistent with this interpretation. Specifically, absorbance bands at 1624 and 1696 $cm^{-1}$ are generally indicative of the presence of beta sheets, whereas an absorbance band at 1657 $cm^{-1}$ is consistent with the presence of alpha helices.

The dissolution of insoluble GLP-1 compounds in aqueous base (or aqueous acid) is consistent with the breakdown of the intramolecular and intermolecular interactions responsible for beta sheet formation. Moreover, the isolation of the soluble form of GLP-1 compounds from these solutions is consistent with the reformation of the secondary structure of soluble GLP-1 compounds. Therefore, the method of the present invention can be used with proteins (e.g., GLP-1 compounds) having a soluble active form characterized by high alpha helix content and an inactive or insoluble form characterized by high beta sheet content to convert from the insoluble to the soluble form.

The method of the present invention can be used to convert insoluble GLP-1 compounds to soluble GLP-1 compounds in compositions wherein the insoluble GLP-1 compound is the only component or, alternatively, wherein the insoluble GLP-1 compound is one of several components. Thus, the method can "purify" mixtures comprising both the soluble and insoluble form of a GLP-1 compound by converting the insoluble form to the soluble form. The method is therefore ideally suited for removing small or even trace amounts of the insoluble form from or minimizing the amount of the insoluble form in the composition before, for example, administration as a drug or formulation into a drug dosage form.

By custom in the art, the amino terminus of GLP-1(7-37)OH has been assigned number residue 7 and the carboxy-terminus, number 37. This nomenclature carries over to other GLP compounds. When not specified, the C-terminal is usually considered to be in the traditional carboxyl form. The amino acid sequence of GLP-1(7-37)OH is provided below:

```
                                          (SEQ ID NO: 1)
⁷His-Ala-Glu-¹⁰Gly-Thr-Phe-Thr-Ser-¹⁵Asp-Val-Ser-

Ser-Tyr-²⁰Leu-Glu-Gly-Gln-Ala-²⁵Ala-Lys-Glu-Phe-

Ile-³⁰Ala-Trp-Leu-Val-Lys-³⁵Gly-Arg-³⁷Gly-COOH
```

A "GLP-1 compound" has sufficient homology to GLP-1 (7-37)OH or a fragment of GLP-1(7-37)OH such that the compound has insulinotropic activity. Preferably, a GLP-1 compound has the amino acid sequence of GLP-1(7-37)OH or a fragment thereof, modified so that from zero, one, two, three, four or five amino acids differ from the amino acid in corresponding position of GLP-1(7-37)OH or the fragment of GLP-1(7-37)OH. Preferred GLP compounds are modified at position 8, at position 22 or at position 8 and position 22.

Preferably, the amino acids in the GLP compound which differ from the amino acid in corresponding position of GLP-1(7-37)OH are conservative substitutions and, more preferably, are highly conservative substitutions.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a GLP-1 compound with another amino acid from the same groups results in a conservative substitution:

Group I: glycine, alanine, valine, leucine, isoleucine, serine, threonine, cysteine, methionine and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Example of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

"GLP-1 analog" is defined as a GLP-1 compound having one or more amino acid substitutions, deletions, inversions, or additions relative to GLP-1(7-37)OH. Permissible amino acid substitutions include the replacing of an L-amino acid with its corresponding D-form. In the nomenclature used herein to designate GLP-1 analogs, the substituting amino acid and its position is indicated prior to the parent structure. For example, Val$^8$-GLP-1(7-37)OH designates a GLP-1 analog in which the alanine normally found at position eight of GLP-1(7-37)OH has been replaced with valine. Numerous GLP-1 analogs are known in the art and include, but are not limited to: GLP-1(7-34), GLP-1(7-35), GLP-1(7-36)NH$_2$, Gln$^9$-GLP-1(7-37), d-Gln$^9$-GLP-1(7-37), Thr$^{16}$-Lys$^{18}$-GLP-1(7-37), Lys$^{18}$-GLP-1(7-37), Gly$^8$-GLP-1(7-36)NH$_2$, Gly$^8$-GLP-1(7-37)OH, Val$^8$-GLP-1(7-36)NH$_2$, Val$^8$-GLP-1(7-37)OH, Met$^8$-GLP-1(7-36)NH$_2$, Met$^8$-GLP-1(7-37)OH, Ile$^8$-GLP-1(7-36)NH$_2$, Ile$^8$-GLP-1(7-37)OH, Thr$^8$-GLP-1(7-36)NH$_2$, Thr$^8$-GLP-1(7-37)OH, Ser$^8$-GLP-1(7-36)NH$_2$, Ser$^8$-GLP-1(7-37)OH, Asp$^8$-GLP-1(7-36)NH$_2$, Asp$^8$-GLP-1(7-37)OH, Cys$^8$-GLP-1(7-36)NH$_2$, Cys$^8$-GLP-1(7-37)OH, Thr$^9$-GLP-1(7-37), D-Thr$^9$-GLP-1(7-37), Asn$^9$-GLP-1(7-37), D-Asn$^9$-GLP-1(7-37), Ser$^{22}$-Arg$^{23}$-Arg$^{24}$-Gln$^{26}$-GLP-1(7-37), Arg$^{23}$-GLP-1(7-37), Arg$^{24}$-GLP-1(7-37), and Gly$^8$-Gln$^{21}$-GLP-1(7-37)OH, and the like.

A "GLP-1 derivative" is defined as a molecule having the amino acid sequence of GLP-1(7-37) or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl (e.g., —CO-lower alkyl) modifications. Modifications of the terminal carboxy group include, without limitation, the amide, lower alkyl amide, dialkyl amide, and lower alkyl ester modifications. Lower alkyl includes straight or branched chain C$_1$-C$_4$ alkyl. Furthermore, one or more side groups, or terminal groups, may be protected by protective groups known to the ordinarily-skilled protein chemist. The α-carbon of an amino acid may be mono- or dimethylated.

Other GLP-1 compounds are described in U.S. Pat. No. 5,705,483 and have the amino acid sequence shown by SEQ ID NO: 2. The entire teachings of U.S. Pat. No. 5,705,483 are incorporated herein by reference.

(SEQ ID NO: 2)
R$_1$-X-Gly-$^{10}$Gly-Thr-Phe-Thr-Ser-$^{15}$Asp-Val-Ser-Ser-

Tyr-$^{20}$Leu-Y-Gly-Gln-Ala-$^{25}$Ala-Lys-Z-Phe-Ile-$^{30}$Ala-

Trp-Leu-Val-Lys-$^{35}$Gly-Arg-R$_2$

R$_1$ in SEQ ID NO: 2 is L-histidine, D-histidine, desamino-histidine, 2-amino-histidine, beta-hydroxy-histidine, homo-histidine, alpha-fluoromethyl-histidine or alpha-methyl-histidine.

X is Ala, Gly, Val, Thr, Met, Ile, Ser or alpha-methyl-Ala.

Y is Glu, Gln, Ala, Thr, Ser or Gly.

Z is Glu, Gln, Ala, Thr, Ser or Gly.

R$_2$ is NH$_2$ or Gly-OH.

Yet other GLP-1 compounds are described in WO 91/11457, the entire teachings of which are incorporated herein by reference. These GLP-1 compounds include GLP-1(7-34), GLP-1(7-35), GLP-1(7-36), or GLP-1(7-37), or the amide form thereof, and pharmaceutically-acceptable salts thereof, having at least one of the following modifications:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26;

(d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; or (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions in (a), (b), (d), and (e), the substituted amino acids can optionally be in the D-form and the amino acids substituted at position 7 can optionally be in the N-acylated or N-alkylated form.

Yet other GLP-1 compounds are disclosed in U.S. Pat. No. 5,188,666, the entire teachings of which are incorporated herein by reference. Examples include a peptide having the amino acid sequence of SEQ ID NO: 3:

```
                                          (SEQ ID NO: 3)
His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-X
``` and pharmaceutically-acceptable salts thereof.

X in SEQ ID NO: 3 is Lys-COOH and Lys-Gly-COOH.

Also included are a pharmaceutically-acceptable lower alkyl ester of said peptide and a pharmaceutically-acceptable amide of said peptide, e.g., lower alkyl amide, and lower dialkyl amide. Generally, lower alkyl groups are a C1-C20 straight chained or branched aliphatic group with zero, one or more units of unsaturation.

Yet other GLP-1 compounds are disclosed in U.S. Pat. No. 5,512,549, the entire teachings of which are incorporated herein by reference. These GLP-1 compounds have the amino acid sequence of SEQ ID NO: 4:

(SEQ ID NO: 4)

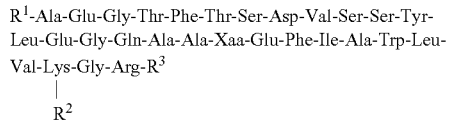

$R^1$ is 4-imidazopropionyl, 4-imidazoacetyl, or 4-imidazo-α, α dimethyl-acetyl.

$R^2$ is $C_6$-$C_{10}$ unbranched acyl or is absent.

$R^3$ is Gly-OH or $NH_2$.

Xaa is Lys or Arg.

Still other GLP-1 compounds are disclosed in WO 98/08871, the entire teachings of which are incorporated herein by reference. These GLP-1 compounds include a lipophilic substituent attached to the N-terminal or to the C-terminal amino acid residue wherein the substituent is an alkyl group or a group which has an omega carboxylic group.

"Biosynthetic GLP-1's" are defined as any GLP-1 analog or native sequence which contain only naturally occurring amino acid residues and are thus capable of being expressed by living cells, including recombinant cells and organisms.

"DPP-IV protected GLP's" refers to GLP-1 compounds which are resistant to the action of DPP-1V. These include analogs having a modified or D amino acid residue in position 8. These also include biosynthetic GLP-1's having Gly or the L amino acid residues Val, Thr, Met, Ser, Cys, Ile, or Asp in position 8. Other DPP-1V protected GLP-1 compounds include des amino His[7] and other His[7] derivatives.

In the method of the present invention, insoluble GLP-1 compound is added to a solution that is sufficiently basic (or acidic) to dissolve the compound. The solution is then mixed or otherwise agitated until the compound dissolves. GLP-1 compounds generally dissolve more rapidly as the basicity or acidity of the solution increases. However, the rate of racemization and other degradation also increases as the solution becomes more basic (or acidic) and the longer a GLP-1 compound is dissolved in highly basic or acidic solution. Therefore, in practicing the method of the present invention, it is desirable to use solutions that are sufficiently basic (or acidic) to readily dissolve the compound but not so basic (or acidic) to result in amino acid racemization or the formation of other by-products. The skilled artisan will be able to routinely identify suitable pHs which will achieve these dual goals. Basic solutions having a pH between about 10.5 and about 12.5 and acidic solutions having a pH between about 1.5 and about 2.0 are typically used for carrying out the method of the present invention. However, less basic solutions can also be used, provided that sufficient period of time is allowed for dissolution. Solutions having a pH between about 10.0 and 10.5 have been used with dissolution times of at least thirty minutes. Preferred are pHs between about 12.1 and about 12.5. In one aspect, it is desirable to minimize the amount of aqueous base or aqueous acid being used to dissolve the GLP-1 compound. A minimum amount of aqueous base or aqueous acid is preferred when the final GLP-1 compound is being isolated by lyophilization.

Following dissolution of the GLP-1 compound, the solution, referred to herein as a "GLP-1 solution", is neutralized to a pH at which substantially no amino acid racemization occurs, e.g., less than 1% of the GLP-1 compound racemizes per hour and preferably less than 0.1%. Amino acid racemization in GLP-1 compounds can be detected and quantitated by methods known in the art such as HPLC chromatography (see, for example, Senderoff et al., *J. Pharm. Sci.* 87:183 (1998)) and the assay described in Example 6. Thus, suitable pHs for the neutralized solution can be readily determined by one of ordinary skill in the art. For most applications, pH values for the neutralized solution can range from between about 6.5 to about 9.0. Preferred pH values are between about 7.0 and about 8.5.

In order to minimize amino acid racemization, it is desirable to neutralize the basic or acidic GLP-1 solution as soon as possible after dissolution of the insoluble GLP-1 compound. Preferably, the GLP-1 solution is neutralized within a sufficiently short period of time so that there is substantially no racemization or degradation of amino acids in the GLP-1 compound, e.g., less than 1% of the GLP-1 compounds contain racemized amino acids and preferably less than 0.1%. As noted above, the rate of amino acid racemization and other degradation increases with increasing solution basicity or acidity. Therefore, the amount of time which can lapse between dissolution and neutralization without the substantial formation of degradation or racemization by-products varies according to the pH of the GLP-1 solution. When the pH of the GLP-1 solution is between about 10.5 and about 12.5 or between about 1.5 and about 2.0, substantially no amino acid racemization or degradation occurs when the GLP-1 solution is neutralized within about thirty minutes after dissolution of the insoluble GLP-1 compound. Preferably, the GLP-1 solution is neutralized within about five minutes after dissolution. Optionally, the GLP-1 solution can be neutralized before complete dissolution of the insoluble GLP-1 compound, provided that the undissolved material is removed from the solution before isolation of the soluble GLP-1 compound. Undissolved material can be removed by any suitable means, including by filtration.

Any suitable acid or base can be used to adjust the pH of a solution in the method of the present invention. Preferably, the acid or base are suitable for use in the preparation of a pharmaceutical product. Examples of suitable acids include hydrochloric acid, sulfuric acid, acetic acid, oxalic acid and the like. Hydrochloric acid is preferred. Examples of suitable bases include hydroxide bases and carbonate bases. Sodium hydroxide is preferred.

A small amount of solid material, referred to herein as "gelatinous material", typically remains undissolved in the GLP-1 solution. It is preferable to remove this material from the GLP-1 solution or the neutralized GLP-1 solution before isolation of the soluble GLP-1 compound. In one example, the pH of the GLP-1 solution is adjusted to about 8.0 before removing the gelatinous material. Removal of gelatinous material can be carried out by any suitable means, including by filtration.

Isolated soluble GLP-1 compound prepared by the method of the present invention can be used as the active ingredient in a pharmaceutical product for the treatment of diseases such as Type II diabetes or obesity. Consequently, it is desirable to remove microbial matter from the GLP-1 solution and/or the neutralized solution. Microbial matter is typically removed from solutions with a suitable filter membrane, preferably with a filter membrane having a porosity less than or equal to 0.22 µM. Filtration steps to remove gelatinous material and microbial material can be combined or, alternatively, performed as separate steps. In addition, it is desirable to carry out the method of the present invention in a sterile environment consistent with Good Manufacturing Practices when the final GLP-1 compound is being used as a pharmaceutical.

Soluble GLP-1 compound can be isolated from the neutralized solution by any suitable method, including by lyophilization, spray drying or crystallization. Examples of a suitable crystallization methods are described in EP 619,322 by Gelfand et al., and WO 99/30731 by Hoffman, et al. The entire relevant teachings of these references are incorporated herein by reference.

Given the sequence information herein disclosed and the state of the art in solid phase protein synthesis, GLP's can be obtained via chemical synthesis. However, it also is possible to obtain some GLP's by enzymatically fragmenting proglucagon using techniques well known to the artisan. Moreover, well known recombinant DNA techniques may be used to express GLP's consistent with the invention and are preferred.

The principles of solid phase chemical synthesis of polypeptides are well known in the art and may be found in general texts in the area such as Dugas, H. and Penney, C., *Bioorganic Chemistry* (1981) Springer-Verlag, New York, pgs. 54-92, Merrifield, J. M., *Chem. Soc.*, 85:2149 (1962), and Stewart and Young, *Solid Phase Peptide Synthesis*, pp. 24-66, Freeman (San Francisco, 1969).

Specific descriptions for the preparation of GLP-1 compounds are provided in U.S. Pat. No. 5,705,483, U.S. Pat. No. 5,188,666, U.S. Pat. No. 5,512,549, WO 91/11457 and WO 98/08871, the entire teachings of which are incorporated herein by reference.

The invention is illustrated by the following examples which are not intended to be limiting in any way.

EXAMPLE 1

Preparation of Val$^8$-GLP(7-37)OH

Val$^8$-GLP-1(7-37)OH having the amino acid sequence H$_2$N-His-Val-Glu-Gly-Thr-Phe-Thr-Ser-Asp-Val-Ser-Ser-Tyr-Leu-Glu-Gly-Gln-Ala-Ala-Lys-Glu-Phe-Ileu-Ala-Trp-Leu-Val-Lys-Gly-Arg-Gly-COOH (SEQ ID NO: 5) was prepared using solid phase peptide synthesis methods and the final product was purified by preparative reversed phase chromatography on a C8 silicon-based resin using 0.1% TFA and an acetonitrile elution gradient. The resultant mainstream was dried by lyophilization. Val$^8$-GLP(7-37) can also be prepared recombinantly according to procedures disclosed in U.S. Pat. No. 5,705,483, the entire teachings of which are incorporated herein by reference.

EXAMPLE 2

Conversion of Soluble GLP-1 and GLP-1 Analogs to the Insoluble Form

A. Conversion of Soluble Val$^8$-GLP(7-37)OH to the Insoluble Form in Aqueous Solution Val$^8$-GLP-1(7-37)OH (1 gram) lyophilized powder was dissolved in 25 mM ammonium bicarbonate, pH 8.0 (100 ml). The solution was stirred with a TEFLON stir bar at about 200 rpm at 21° C. (ambient temperature) for 16 hours. At varying times, usually within 30 minutes, the solution became hazy. On continued stirring, the haze became visibly more dense. The kinetics of the turbidity were measured by rate of formation of turbidity, i.e. absorbance at 340 nm. The precipitated protein was harvested either by filtration, e.g. Whatman 1 filter disc, or centrifugation. The supernatant was assayed for protein content either by Biuret Colorimetric Assay obtained from Pierce (Rockford, Ill.) or UV absorbance at 280 nm. By either method, the protein precipitate constituted in excess of 90% of the starting material, i.e. there was less than 10% of the protein remaining in the supernatant fraction. The collected precipitate was dried in vacuo, i.e. in a lyophilizer. The resultant precipitated (0.96 grams) material was soluble in 20 mM phosphate at pH 7.2 at less than 0.01 mg/ml. Solubility was tested by suspension of the solid in the buffer, adjustment of pH, if necessary, and filtration through a 0.2 micron filter. The protein content of the filtrate was tested by either Biuret Colorimetric Assay, UV absorbance at 280 nm, or by high pressure liquid chromatography analysis (HPLC) analysis. The HPLC analysis was carried out using a C-18, 5 micron, 300 angstrom silica column (Jupiter C-18 column, obtained from Phenomenex, Torrance, Calif.) and an elution gradient with Buffer A (10% Acetonitrile in 0.1% Trifluoroacetic Acid solution) and Buffer B (90% Acetonitrile in 0.1% Trifluoroacetic Acid solution), 25 to 60% Buffer B over thirty minutes. The column was run at 60° C. at 1.0 ml/min flow rate, detection was at 214 nanometers wavelength and the injection volume was 20 microliters.

GLP compounds (GLP-1(7-37)OH, Val$^8$-GLP(7-37)OH and isopropylimidazole$^7$-arginine$^{26}$-GLP-1(8-37)OH) prepared in this way had a solubility less than 0.1 mg/ml and usually lower than 0.05 mg/ml. Salt, especially sodium chloride, when present at greater than 25 mM greatly accelerated the rate of formation of the insoluble material.

B. Effect of Stirring on Conversion of Soluble Val$^8$-GLP (7-37)OH to the Insoluble Form over Time Three different lots of Val$^8$-GLP-1(7-37)OH (QIY 17, QIY 18 and 361EM7) were solubilized at 1 mg/ml in 20 mM phosphate, pH 7.4 and the final pH adjusted to 7.4 with 1 N sodium hydroxide. Two to ten milliliter samples of each solution were transferred to two different sets of glass vials. One set of samples was stirred while the other was allowed to stand without stirring. The turbidity at varying times was measured by determining the absorbance at 340 nm. The results are shown in The FIGURE. Time courses of stirred solutions are designated with an "s".

As can be seen from The FIGURE, turbidity of the stirred solutions increases far more rapidly in the stirred solutions than in solutions that were allowed to stand. Because turbidity is indicative of protein precipitation, this result is consistent with the rate of formation of the insoluble form being accelerated by increased exposure to air caused by stirring.

C. Conversion of Soluble Val$^8$-GLP-1(7-37)OH to the Insoluble Form by Tangential Flow Val$^8$-GLP(7-37)OH was subjected to filtration by tangential flow. During filtration, the retentate solution thickened and became more viscous and Val$^8$-GLP(7-37)OH formed a gelatinous material on the filter membranes. The formation of the gelatinous material occurred within 30 minutes of starting the filtration; the rate of formation was increased in the presence of salt. The "insolubilized" protein was collected by filtration or centrifugation and dried in a vacuum oven or a lyophilizer. Precipitation in the presence or absence of salt produced a product which was soluble at less than 0.1 mg/ml in a neutral pH buffer.

D. Conversion of Soluble Val$^8$-GLP-1(7-37)OH to the Insoluble Form in Acetic Acid/Acetonitrile Val$^8$-GLP-1(7-37)OH incubated at between 2° to 6° C. in a matrix of 35 mM acetic acid with 25% acetonitrile, apparent pH 3.3. With no stirring, preparations developed gelatinous occlusions over about 1 month incubation. Agitation increased the rate of gel formation. The gel was collected by centrifugation and dried in vacuo and displayed a solubility of less than 0.1 mg/ml at neutral pH.

EXAMPLE 3

Secondary Structure of Soluble and Insoluble Val$^8$-GLP-1(7-37)OH

Four different batches of purified, lyophilized Val-8 GLP-1(7-37)OH were analyzed for secondary structure characteristics by Fourier Transform Infra-red Spectroscopy (FTIR) to assess alpha helix and beta sheet content of the preparations. Deconvolution was done on the Amide I region (1750-1600 cm$^{-1}$) using BioRad Win-1R Pro Software version 2.5. The results are shown below in the Table 1:

TABLE 1

| Batch Number | 1657 cm$^{-1}$ Alpha helix, % | 1624 + 1696 cm$^{-1}$ total beta sheet, % |
|---|---|---|
| 1 | 62.7 | 31.4 |
| 2 | 62.8 | 29.3 |
| 3 | 63.6 | 30.6 |
| 4 | 63.6 | 28.9 |
| MEAN | | 30.1 |
| Sigma | | 1.2 |

The data in the Table show that the lyophilized powder has high alpha helix content (over 60%) and a relatively low beta sheet content (30% or less).

EXAMPLE 4

Conversion of Insoluble Val$^8$-GLP-1(7-37)OH to Soluble Val$^8$-GLP-1(7-37)OH by Base Excursion Five samples of Val$^8$-GLP-1(7-37)OH were prepared as described below:

Sample 1

Lyophilized powder of Val$^8$-GLP-1(7-37)OH was dissolved in 10 mM acetic acid (pH 3) at 1 mg/ml and subjected to isoelectric precipitation by pH adjustment to 5.5 with 1N sodium hydroxide. The resultant precipitate was collected by centrifugation and dried in vacuo.

Sample 2

An isoelectric precipitate was carried out by approaching pH 5.5 from the alkaline side by solubilizing Val$^8$-GLP-1(7-37)OH in 10 mM ammonium bicarbonate, pH 8.0, then adjusting the pH down with 1 N hydrochloric acid.

Sample 3

A gelled sample was collected by centrifugation from a solution of Val$^8$-GLP-1(7-37)OH (2.7 mg/ml in 25 mM Acetic Acid, pH 3.3 containing 25% acetonitrile) which had been incubated at 4° C. for 3.1 months.

Samples 4 and 5

Val$^8$-GLP-1(7-37)OH was dissolved at 1 mg/ml in 10 mM phosphate (pH 7.2) and stirred until a precipitate formed. The solution was fractionated by centrifugation to produce a soluble GLP-1 fraction (Sample 4) and a precipitated fraction (Sample 5). Both fractions were dried in vacuo.

Each of Samples 1-5 was measured for secondary structure characteristics by Fourier Transform Infrared Spectroscopy (FTIR). In addition, each Sample 1-5 was placed into 20 mM phosphate solution (pH 7.2) and the pH raised to 12.3 by addition of 1N sodium hydroxide for no more than 3 minutes. All samples then dissolved and the solutions became clear. The pH of each solution was then adjusted to 7.0 by addition of 1N hydrochloric acid. Samples 1A-5A, obtained from Samples 1-5, respectively, were then obtained by lyophilization of the solutions and dried in vacuo. The secondary structural characteristics of Samples 1A-5A were assessed by FTIR. The results of the FTIR analysis of Samples 1-5 and 1A-5A are shown below in Table 2:

TABLE 2

| Sample | alpha helix percent 1657 cm$^{-1}$ | beta sheet character percent 1624 + 1696 cm$^{-1}$ |
|---|---|---|
| 1 | 24.9 | 69.8 |
| 1A | broad peak at 1583 cm$^{-1}$ interfered with analysis | |
| 2 | 51.9 | 40.5 |
| 2A | 85.9 | none observed |
| 3 | 25.5 | 70.0 |
| 3A | 62.2 | 23.7 |
| 4 | 75.8 | 14.7 |
| 4A | 86.0 | none observed |
| 5 | 12.9 | 57.3 |
| 5A | 90.6 | none observed |

All samples were analyzed by High Performance Liquid Chromatography, as described in Example 2 and shown to contain a single peak which co-eluted with reference to standard Val$^8$-GLP-1(7-37)OH. This suggests that no sample underwent an HPLC discernible chemical change. In each case, the base excursion increased the measured alpha helix content of the protein and resulted in a product which was soluble at >1 mg/ml in 20 mM phosphate buffer, pH 7.2.

In another example of the effects of base excursion on secondary structure, a purified, lyophilized sample of Val$^8$-GLP-1(7-37)OH purified by reversed chromatography was either lyophilized (0.1 gram) or precipitated by addition of sufficient 3.0 M sodium dihydrogen phosphate (pH 3.80) to result in a 0.6 M phosphate solution. The resultant precipitate was washed with 10 mM sodium acetate at pH 5.5 and the washed precipitate was dried in vacuo. A second portion of the washed precipitate was solubilized by raising the pH of the material to 10.5 for 30 minutes at room temperature by addition of 1N sodium hydroxide. The pH of that solution was then reduced to 7.0 by addition of 1.0 N hydrochloric acid and the solution was then lyophilized. The secondary structure of the three samples was determined by FTIR. The results are shown in Table 3:

TABLE 3

| Sample | percent alpha helix content | percent beta sheet content |
|---|---|---|
| Lyophilized mainstream | 71 | 16 |
| Phosphate precipitate | 57 | 35 |
| pH 10.5 excursion | 71 | 13 |

The results show that basic pH excursion reduces the beta sheet content and increases the alpha helix content of the sample.

EXAMPLE 5

Soluble Val$^8$-GLP-1(7-37)OH Showed Increased Bioavailability Compared with Insoluble Val$^8$-GLP-1(7-37)OH High beta sheet-content Val$^8$-GLP-1(7-37)OH was prepared by solubilization of the lyophilized powder in 20 mM phosphate buffer, pH 7.2 and subjecting the solution to stirring overnight at 21° C. The resultant precipitate was collected, washed with de-ionized water and dried in vacuo. The lyophilized powder starting material and the dried, precipitate were tested for bioavailability by injection into groups of three rats. To prepare the samples, the lyophilized powder starting material (soluble) was formulated into a solution at 2 mg/mL in 15 mM phosphate buffer (pH 7.5). The dried precipitate was then made into a slurry in 10 mM phosphate (pH 7.2); the insoluble material was made into a suspension at 16.5 mg solid per mL in 15 mM phosphate buffer (pH 7.5). The formulated materials were injected subcutaneously at 80 and 800 microgram/kilogram body weight, while the precipitate slurry was injected at 10 times that, i.e. 8000 micrograms/kilogram. The maximum concentration in serum samples taken from the rats was determined by Enzyme Linked Immunoabsorbent Assay to be 11-15 nanogram/ml for the formulated material and 0.4 to 0.6 ng/ml for the slurry. The area under the curve was about 1% or less for the slurry as compared to the formulated material.

EXAMPLE 6

HPLC Analysis of Val$^8$-GLP-1(7-37)OH Exposed to High pH for Short Periods

Solubilized Val$^8$-GLP-1(7-37)OH was exposed to pH 12.3 for 10 minutes at room temperature. No discernible change was observed in the HPLC profile. However, an HPLC analysis, performed as described in Example 2, of solubilized Val$^8$-GLP-1(7-37)OH, exposed to pH 12.3 for several hours, showed several new peaks which were more polar, i.e., eluted earlier. Three new peaks were prominent in this profile and grew at 0.36, 0.06 and 0.64% per hour. A five minute exposure would result in 0.09% degradation according to this data. Fractionation of these peaks and analysis by mass spectroscopy (ESI) and Edman degradation analysis showed the three peaks have identical masses (3384.4+/−0.5 amu) and sequences through the 31 cycles of the peptides. This result is consistent with the isomerization of amino acid residues from the L to the D conformation (see, for example, Senderoff, et al., *J. Pharm. Sci.* 87:183 (1998).

This data is consistent with the conclusion that the currently observed conformational effects of base excursion on Val$^8$-GLP-1(7-37)OH, as measured by FTIR and solubility, are not due to L to D isomerization, which is manifest in new HPLC peaks.

EXAMPLE 7

Conversion of Insoluble Val$^8$-GLP-1(7-37)OH to Soluble Val$^8$-GLP-1(7-37)OH by Acid Excursion Insoluble Val$^8$-GLP-1(7-37)OH was suspended in de-ionized water at 2 mg solid/ml. The pH of one aliquot was dropped to 1.74 by addition of 12 microliters of 85% phosphoric acid/ml solution. The pH of a second aliquot was dropped to pH 1.92 by addition of 5.5 microliters of 10% hydrochloric acid/ml solution. Each sample was gently stirred for 15 minutes. The samples were adjusted to pH 7.4 by addition of 10% sodium hydroxide and then each was filtered through a 0.2 micron filtered membrane. The soluble portion was lyophilized and analyzed for secondary structure. Infrared analysis of the products showed that the major absorbance in the amide region to be at 1657 cm$^{-1}$, consistent with the formation of soluble Val$^8$-GLP-1(7-37)OH. HPLC analysis, as described in Example 6, showed no detectable racemization.

Recovered yield was 77.5% for the hydrochloric acid treated sample and 6.4% for the phosphoric acid treated sample.

Those skilled in the art will be able to recognize, or be able to ascertain, using no more than routine experimentation, many equivalents to the specific embodiments of the invention described herein. Such equivalents are intended to be encompassed by the following claims.

---

What is claimed is:

1. A method of preparing a Glucagon-Like Peptide 1 (GLP-1) compound that is soluble in aqueous solution at pH 7.4, said GLP-1 compound being referred to as a "soluble GLP-1 compound", from the corresponding GLP-1 compound that is insoluble in aqueous solution at pH 7.4, said GLP-1 compound being referred to as an "insoluble GLP-1" compound, said method comprising the steps of:

a) dissolving the insoluble GLP-1 compound in aqueous base to a pH between 10.5 and 12.5 or in aqueous acid to a pH between 1.5 and 2.0 to form a GLP-1 solution;

b) neutralizing the GLP-1 solution to a pH between 6.5 and 9.0 at which no amino acid racemization of the dissolved GLP-1 compound occurs; and c) isolating soluble GLP-1 compound from the neutralized solution of step b).

2. The method of claim 1 wherein the insoluble GLP-1 compound is GLP-1(7-34), GLP-1(7-35), GLP-1(7-36), or GLP-1(7-37), or the amide form thereof, having at least one of the following modifications:

a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36.

3. The method of claim 1 wherein the insoluble GLP-1 compound is GLP-1(7-34), GLP-1(7-35), GLP-1(7-36), or GLP-1(7-37), or the amide form thereof, having at least one of the following modifications:
   a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;
   b) substitution of an oxidation-resistant amino acid for tryptophan at position 31;
   c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26;
   d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; or
   e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions in a), b), d), and e), the substituted amino acids can optionally be in the D-form and the amino acids substituted at position 7 can optionally be in the N-acylated or N-alkylated form.

4. The method of claim 1 wherein the pH of the aqueous base of step his between 12.1 and 12.5 and the pH of the neutralized solution of step b) is between 7.0 and 8.5.

5. The method of claim 1 wherein the pH of the neutralized solution of step b) is between 7.0 and 8.5.

* * * * *

UNITED STATES PATENT AND TRADEMARK OFFICE
CERTIFICATE OF CORRECTION

| | | |
|---|---|---|
| PATENT NO. | : 8,222,205 B2 | Page 1 of 1 |
| APPLICATION NO. | : 12/551841 | |
| DATED | : July 17, 2012 | |
| INVENTOR(S) | : Walter Francis Prouty, Jr. | |

It is certified that error appears in the above-identified patent and that said Letters Patent is hereby corrected as shown below:

On the Title page, column 2, line 1, Item (56) Other Publications, delete "Near-Infared" and insert -- Near-Infrared--, On the Title page, column 2, line 10, Item (56) Other Publications, delete "duging" and insert -- during --, In the Specifications Column 1, lines 4-9, should read "This application is a continuation of U.S. Application No. 10/169,657, now U.S. Patent No. 7,598,222, filed 01/16/2001, which claims the priority of U.S. Provisional Application Nos. 60/178,438, filed 01/27/2000 and 60/224,058, filed 09/09/2000.", In the Claims Column 36, line 17, Claim 4, delete "his" and insert -- a) is --.

Signed and Sealed this
Eighteenth Day of February, 2014

Michelle K. Lee
*Deputy Director of the United States Patent and Trademark Office*

SEQUENCE LISTING

```
<160> NUMBER OF SEQ ID NOS: 36

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
```

```
<222> LOCATION: (1)..(1)
<223> OTHER INFORMATION: X at position 1 is L-histidine, D-histidine,
      desamino-histidine, 2-amino-histidine, beta-hydroxy-histidine,
      homohistidine, alpha-fluoromethyl-histidine or alpha-methyl-
      histidine
<220> FEATURE:
<221> NAME/KEY: VARIANT
<222> LOCATION: (2)..(2)
<223> OTHER INFORMATION: X at position 2 is Ala, Gly, Val, Thr, Met,
      Ile, Ser or alpha-methyl-Ala
<220> FEATURE:
<221> NAME/KEY: VARIANT
<222> LOCATION: (15)..(15)
<223> OTHER INFORMATION: X at position 15 is Glu, Gln, Ala, Thr, Ser
      or Gly
<220> FEATURE:
<221> NAME/KEY: VARIANT
<222> LOCATION: (21)..(21)
<223> OTHER INFORMATION: X at position 21 is Glu, Gln, Ala, Thr, Ser
      or Gly
<220> FEATURE:
<221> NAME/KEY: VARIANT
<222> LOCATION: (31)..(31)
<223> OTHER INFORMATION: X at position 31 is NH2 or Gly-OH

<400> SEQUENCE: 2

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Xaa
            20                  25                  30

<210> SEQ ID NO 3
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (28)..(28)
<223> OTHER INFORMATION: X at position 28 is Lys-COOH and Lys-Gly-COOH

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa
            20                  25

<210> SEQ ID NO 4
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (1)..(1)
<223> OTHER INFORMATION: X at position 1 is 4-imidazopropionyl,
      4-imidazoacetyl, or 4-imidazo-a, a dimethyl-acetyl
<220> FEATURE:
<221> NAME/KEY: VARIANT
<222> LOCATION: (20)..(20)
<223> OTHER INFORMATION: X at position 20 is Lys or Arg
<220> FEATURE:
<221> NAME/KEY: VARIANT
<222> LOCATION: (28)..(28)
<223> OTHER INFORMATION: X at position 28 is Lys or is Lys-C6-C10
      unbranched acyl
<220> FEATURE:
<221> NAME/KEY: VARIANT
<222> LOCATION: (31)..(31)
<223> OTHER INFORMATION: X at position 31 is Gly-OH or NH2

<400> SEQUENCE: 4
```

```
Xaa Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Xaa Gly Arg Xaa
            20                  25                  30

<210> SEQ ID NO 5
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Position 2 is Val

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 28
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (1)..(28)
<223> OTHER INFORMATION: The last 3 amino acids of GLP-1 (7-37) are
      deleted

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

<210> SEQ ID NO 7
<211> LENGTH: 29
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (1)..(29)
<223> OTHER INFORMATION: The last 2 amino acids of GLP-1 (7-37) are
      deleted

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 8
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X at position 3 is Gln
```

```
<400> SEQUENCE: 8

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 9
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X at position 3 is d-Gln

<400> SEQUENCE: 9

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 10
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (10)..(10)
<223> OTHER INFORMATION: X at position 10 is Thr
<220> FEATURE:
<221> NAME/KEY: VARIANT
<222> LOCATION: (12)..(12)
<223> OTHER INFORMATION: X at position 12 is Lys

<400> SEQUENCE: 10

His Ala Glu Gly Thr Phe Thr Ser Asp Xaa Ser Xaa Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 11
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (12)..(12)
<223> OTHER INFORMATION: X at position 12 is Lys

<400> SEQUENCE: 11

His Ala Glu Gly Thr Phe Thr Ser Asp Val Ser Xaa Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 12
<211> LENGTH: 31
<212> TYPE: PRT
<213> ORGANISM: Artificial
<220> FEATURE:
<223> OTHER INFORMATION: synthetic construct
```

```
<220> FEATURE:
<221> NAME/KEY: VARIANT
<222> LOCATION: (2)..(2)
<223> OTHER INFORMATION: X at position 2 is Gly
<220> FEATURE:
<221> NAME/KEY: VARIANT
<222> LOCATION: (31)..(31)
<223> OTHER INFORMATION: X at position 31 is NH2

<400> SEQUENCE: 12

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 13
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Gly

<400> SEQUENCE: 13

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 14
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Val
<220> FEATURE:
<221> NAME/KEY: VARIANT
<222> LOCATION: (31)..(31)
<223> OTHER INFORMATION: X at position 31 is NH2

<400> SEQUENCE: 14

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 15
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Val

<400> SEQUENCE: 15

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 16
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Met
<220> FEATURE:
<221> NAME/KEY: VARIANT
<222> LOCATION: (31)..(31)
<223> OTHER INFORMATION: X at position 31 is NH2

<400> SEQUENCE: 16

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 17
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Met

<400> SEQUENCE: 17

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 18
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Ile
<220> FEATURE:
<221> NAME/KEY: VARIANT
<222> LOCATION: (31)..(31)
<223> OTHER INFORMATION: X at position 31 is NH2

<400> SEQUENCE: 18

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 19
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Ile

```
<400> SEQUENCE: 19

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 20
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Thr
<220> FEATURE:
<221> NAME/KEY: VARIANT
<222> LOCATION: (31)..(31)
<223> OTHER INFORMATION: X at position 31 is NH2

<400> SEQUENCE: 20

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 21
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Thr

<400> SEQUENCE: 21

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 22
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Ser
<220> FEATURE:
<221> NAME/KEY: VARIANT
<222> LOCATION: (31)..(31)
<223> OTHER INFORMATION: X at position 31 is NH2

<400> SEQUENCE: 22

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 23
<211> LENGTH: 31
```

<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Ser

<400> SEQUENCE: 23

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 24
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Asp
<220> FEATURE:
<221> NAME/KEY: VARIANT
<222> LOCATION: (31)..(31)
<223> OTHER INFORMATION: X at position 31 is NH2

<400> SEQUENCE: 24

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 25
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Asp

<400> SEQUENCE: 25

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 26
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Cys
<220> FEATURE:
<221> NAME/KEY: VARIANT
<222> LOCATION: (31)..(31)
<223> OTHER INFORMATION: X at position 31 is NH2

<400> SEQUENCE: 26

His Xaa Glu Gly Thr Phe Thr Ser Asp Val Ser Ser Tyr Leu Glu Gly

```
                1               5                   10                  15
Gln Ala Ala Lys Glu Phe Ile Ala Trp Leu Val Lys Gly Arg Xaa
            20                  25                  30

<210> SEQ ID NO 27
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Cys

<400> SEQUENCE: 27

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 28
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X at position 3 is Thr

<400> SEQUENCE: 28

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 29
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X at position 3 is D-Thr

<400> SEQUENCE: 29

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 30
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X at position 3 is Asn

<400> SEQUENCE: 30

His Ala Xaa Gly Thr Phe Thr Ser Asp Val Ser Ser Tyr Leu Glu Gly
```

```
                1               5                  10                 15
Gln Ala Ala Lys Glu Phe Ile Ala Trp Leu Val Lys Gly Arg Gly
                20                 25                 30

<210> SEQ ID NO 31
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: X is position 3 is D-Asn

<400> SEQUENCE: 31

His Ala Xaa Gly Thr Phe Thr Ser Asp Val Ser Ser Tyr Leu Glu Gly
1               5                  10                 15

Gln Ala Ala Lys Glu Phe Ile Ala Trp Leu Val Lys Gly Arg Gly
                20                 25                 30

<210> SEQ ID NO 32
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: X at position 16 is Ser
<220> FEATURE:
<221> NAME/KEY: VARIANT
<222> LOCATION: (17)..(17)
<223> OTHER INFORMATION: X at position 17 is Arg
<220> FEATURE:
<221> NAME/KEY: VARIANT
<222> LOCATION: (18)..(18)
<223> OTHER INFORMATION: X at position 18 is Arg
<220> FEATURE:
<221> NAME/KEY: VARIANT
<222> LOCATION: (20)..(20)
<223> OTHER INFORMATION: X at position 20 is Gln

<400> SEQUENCE: 32

His Ala Glu Gly Thr Phe Thr Ser Asp Val Ser Ser Tyr Leu Glu Xaa
1               5                  10                 15

Xaa Xaa Ala Xaa Glu Phe Ile Ala Trp Leu Val Lys Gly Arg Gly
                20                 25                 30

<210> SEQ ID NO 33
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (17)..(17)
<223> OTHER INFORMATION: X at position 17 is Arg

<400> SEQUENCE: 33

His Ala Glu Gly Thr Phe Thr Ser Asp Val Ser Ser Tyr Leu Glu Gly
1               5                  10                 15

Xaa Ala Ala Lys Glu Phe Ile Ala Trp Leu Val Lys Gly Arg Gly
                20                 25                 30

<210> SEQ ID NO 34
<211> LENGTH: 31
```

```
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (18)..(18)
<223> OTHER INFORMATION: X at position 18 is Arg

<400> SEQUENCE: 34

His Ala Glu Gly Thr Phe Thr Ser Asp Val Ser Ser Tyr Leu Glu Gly
1               5                   10                  15

Gln Xaa Ala Lys Glu Phe Ile Ala Trp Leu Val Lys Gly Arg Gly
            20                  25                  30

<210> SEQ ID NO 35
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: X at position 2 is Gly
<220> FEATURE:
<221> NAME/KEY: VARIANT
<222> LOCATION: (15)..(15)
<223> OTHER INFORMATION: X at position 15 is Gln

<400> SEQUENCE: 35

His Xaa Glu Gly Thr Phe Thr Ser Asp Val Ser Ser Tyr Leu Xaa Gly
1               5                   10                  15

Gln Ala Ala Lys Glu Phe Ile Ala Trp Leu Val Lys Gly Arg Gly
            20                  25                  30

<210> SEQ ID NO 36
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (31)..(31)
<223> OTHER INFORMATION: X at position 31 is NH2

<400> SEQUENCE: 36

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30
```